United States Patent
Xuan et al.

(10) Patent No.: US 9,810,615 B2
(45) Date of Patent: Nov. 7, 2017

(54) CALIBRATION METHOD FOR THE BRITTLE FRACTURE ASSESSMENT PARAMETERS FOR MATERIALS BASED ON THE BEREMIN MODEL

(71) Applicant: East China University of Science and Technology, Shanghai (CN)

(72) Inventors: Fuzhen Xuan, Shanghai (CN); Yupeng Cao, Shanghai (CN); Hu Hui, Shanghai (CN); Penning Li, Shanghai (CN); Guozhen Wang, Shanghai (CN)

(73) Assignee: East China University of Science and Technology, Shanghai (CN)

( * ) Notice: Subject to any disclaimer, the term of this patent is extended or adjusted under 35 U.S.C. 154(b) by 743 days.

(21) Appl. No.: 14/365,273

(22) PCT Filed: Nov. 27, 2012

(86) PCT No.: PCT/CN2012/085336
§ 371 (c)(1),
(2) Date: Jun. 13, 2014

(87) PCT Pub. No.: WO2013/086933
PCT Pub. Date: Jun. 20, 2013

(65) Prior Publication Data
US 2014/0372060 A1 Dec. 18, 2014

(30) Foreign Application Priority Data
Dec. 13, 2011 (CN) .......................... 2011 1 0415419

(51) Int. Cl.
G06F 11/30 (2006.01)
G01N 3/62 (2006.01)
(Continued)

(52) U.S. Cl.
CPC ................. *G01N 3/62* (2013.01); *G01N 3/40* (2013.01); *G06F 17/5018* (2013.01);
(Continued)

(58) Field of Classification Search
None
See application file for complete search history.

(56) References Cited

U.S. PATENT DOCUMENTS

| 7,016,825 | B1 * | 3/2006 | Tryon, III | ........... G06F 17/5018 702/182 |
| 7,992,449 | B1 * | 8/2011 | Mahmoud | ................ G01N 3/08 73/828 |
| 2007/0060465 | A1 | 3/2007 | Varshneya et al. | |

FOREIGN PATENT DOCUMENTS

CN 102494940 A 6/2012

OTHER PUBLICATIONS

International Search Report, 5 Pages dated Mar. 7, 2013.

\* cited by examiner

*Primary Examiner* — Aditya Bhat
(74) *Attorney, Agent, or Firm* — William H. Honaker; Dickinson Wright PLLC

(57) ABSTRACT

A calibration method for brittle fracture assessment parameters for pressure vessel materials based on the Beremin model includes selecting at least two types of specimens of different constraints, and calculating the fracture toughness values $K_0$ corresponding to 63.2% failure probability for each type of specimens at a same calibration temperature by using the respective fracture toughness data. The method proceeds by obtaining the stress-strain curve of the material at the calibration temperature, generating finite element models for each type of specimens, and calculating the maximum principal stress and element volume of every element at $K=K_0$ in each model. A series of values of m are
(Continued)

assumed to compute a group of $\sigma_u$ values for each type of specimens, and then m~$\sigma_u$ curves are plotted for each type of specimens. Brittle fracture assessment parameters are then determined for the material according to the coordinates of the intersection of the m~$\sigma_u$ curves.

10 Claims, 4 Drawing Sheets

(51) Int. Cl.
  *G01N 3/40* (2006.01)
  *G06F 17/50* (2006.01)
(52) U.S. Cl.
  CPC ............... *G01N 2203/0067* (2013.01); *G01N 2203/021* (2013.01); *G01N 2203/0218* (2013.01)

CALIBRATION METHOD FOR THE BRITTLE FRACTURE ASSESSMENT PARAMETERS FOR MATERIALS BASED ON THE BEREMIN MODEL

CROSS REFERENCE TO RELATED APPLICATION

This application claims the benefit of PCT International Application Serial No. PCT/CN2012/085336 filed on Nov. 27, 2012 and entitled a "Method for Calibration of Parameters Assessing Brittle Fracture of Material Based on Beremin Model", which claims the benefit of CN 201110415419.X filed on Dec. 13, 2011, the entire disclosures of which are hereby incorporated by reference.

BACKGROUND OF THE INVENTION

1. Field of the Invention

The invention belongs to the field of pressure vessel and safety engineering, in particular to a calibration method for the brittle fracture assessment parameters for materials, which is a calibration method for the brittle fracture assessment parameters for pressure vessel materials based on the Beremin cleavage fracture model.

2. Related Art

Nuclear power has become an important part of the world's energy structure. Currently, there are 11 reactors in use in our country. In accordance with China's medium and long-term development plan of "Developing Nuclear Power Actively", there will be more than 40 new reactors which are the third generation million-kilowatt advanced pressurized water reactor nuclear power plants as the representative of AP1000 in 15 years. Our country will develop the nuclear power most rapidly in the world. As the key component of the nuclear power plant, reactor pressure vessel is made of ferritic steel, which demonstrates a strong transition phenomenon from ductile to brittle. During service, the steel in the reactor pressure vessel beltline region is subject to neutron irradiation, which results in an upward shift in the transition temperature. In other words, the fracture toughness of the steels decreases within the specified operating temperature. It is very necessary to ensure the structural integrity assessment of the pressure vessels, especially the reactor pressure vessels, under the different possible conditions in the design, operation and maintenance stages to prevent any possible brittle fracture. The fracture toughness of materials (including the base, weld and heat-affected zone materials) is essential to the structural integrity assessment.

Local approach to cleavage fracture is a primary method for predicting brittle failure probability for ferritic pressure vessel steel. Among them, the most widely applied model is the Beremin model which has been included in the famous R6 Procedure "Assessment of the Integrity of Structures Containing Defects". The Beremin model was originally proposed by the research group F.M Beremin for studying cleavage fracture of pressure vessel steels. The Beremin model is very applicable to the analysis of the effect of constraint on cleavage fracture toughness and to the prediction of cleavage fracture of steels subjected to complex loading conditions such as multi-axial loading and high strain rate loading.

The Beremin model uses only two parameters, the Weibull slope m and Weibull scale parameter $\sigma_u$, to describe the complex cleavage fracture events. Therefore, the applicability of the Beremin model to predict cleavage fracture in structures relies heavily on the model's parameters. The calibration method for Beremin model's parameters is a key technology for the brittle fracture assessment procedure for pressure vessel materials.

Several calibration methods have been reported in the literatures. For example, in 1992, Minami et al published "Estimation procedure for the Weibull stress parameters used in the local approach" in the journal "International Journal of Fracture", in which a calibration method using a maximum likelihood analysis of a single set of fracture toughness values for high constraint specimens was proposed; in 1998, a paper entitled "Calibration of Weibull stress parameters using fracture toughness data" published by Gao et al in the journal "Engineering fracture mechanics" first describes a calibration method (GRD method) based on the analysis of two sets of fracture toughness values exhibiting different constraint levels at fracture; in 2000, Ruggieri et al's (RGD) paper "Transferability of elastic-plastic fracture toughness using the Weibull stress approach: significance of parameter calibration" published in the journal "Engineering Fracture Mechanics" simplifies the GRD method.

However, the existing methods require a lot of complex calculations and sometimes a specialized computer program. In particular, the calibration method proposed by Minami et al must need a specialized computer program that employs an iterative process to obtain m and $\sigma_u$. When the RGD method is utilized, the maximum principal stress and volume of every element first need to be extracted from the fracture process region of each model at different loading levels, assume several trial values of m and do a lot of calculations to build the $\sigma_w$ vs. $K_J$ relationships for each type of specimens using the exported data, and finally construct the toughness scaling diagrams between the two different specimens based on equal $\sigma_w$ values. The method is computationally expensive.

In addition, the calibration method proposed by Minami et al is based on the analysis of a single set of fracture toughness data for high constraint specimen, which results in large uncertainty in the calibrated Beremin model's parameters and poor transferability of the calibrated parameters across structures of different constraints. The RGD calibration and the GRD calibration method determine parameters (m, $\sigma_u$) using two sets of fracture toughness data obtained for high constraint and low constraint specimens, but can't tune (m, $\sigma_u$) by using more than two types of specimens simultaneously. Moreover, when there are equivalent solutions for the model's parameters, the GRD calibration method and the RGD calibration method only give the most accurate solution for the parameters (m, $\sigma_u$), but neglect the other solutions.

SUMMARY OF THE INVENTION

Aiming at the problems and shortcomings of the calibration method of Beremin model parameters in prior art, the invention provides a simplified calibration method for the parameters based on the intersection of m~$\sigma_u$ curves for the specimens of different constraints. The method can easily determine Beremin model's parameters by using simultaneously several types of specimens of different constraints without affecting the calibration precision. And both the accurate solution and the equivalent solutions for the Beremin model's parameters can be obtained.

A calibration method for the brittle fracture assessment parameters for materials based on the Beremin model according to the present invention comprises the following steps:

(1) Selecting at least two types of specimens made of a same material but with different constraints, and calculating the fracture toughness value $K_0$ corresponding to 63.2% failure probability for each type of specimens at a same calibration temperature by using the respective fracture toughness data;

(2) Constructing finite element models for each type of specimens using the stress-strain curve of the material measured at the same calibration temperature, and calculating the maximum principal stress $\sigma_{1,i}$ and element volume $V_i$ of each element in each model at $K=K_0$, where K is a stress intensity factor that describes the intensity of far field loading on the crack front, and i is an order number of elements;

(3) Assuming a series of values of the Weibull slope m and calculating a set of values of the Weibull scale parameter $\sigma_u$ for each type of specimens according to the following equation, and plotting the Beremin's parameter characteristic curves for each type of specimens, i.e. the curves representing the relationship between m and $\sigma_u$ for each type of specimens;

$$\sigma_u = \sqrt[m]{\sum_{i}^{n} (\sigma_{1,i})^m \frac{V_i}{V_0}}$$

wherein, n represents the number of elements in the fracture process region, $V_0$ represents a reference volume;

(4) Determining the brittle fracture assessment parameters for the material according to the coordinates of the intersection of the Beremin's parameters characteristic curves.

Comparing with the GRD calibration method and the RGD calibration method, the calibration method proposed in the invention eliminates the redundant calculations of the $\sigma_w$ and the toughness scaling based on equal $\sigma_w$ values in the case of $K_j \neq K_0$, but only need to compute the values of $\sigma_u$ at $K=K_0$ using the assumed m values. The calibration procedure does not affect the calibration precision of Beremin model's parameters, and the values of m and $\sigma_u$ can be obtained simultaneously. The calibration method provided by the present invention visually displays the convergence process of calibration. The solutions for (m, $\sigma_u$) can be determined through the different cases of intersection of m~$\sigma_u$ curves: if there is only one point of intersection, it indicates that a single solution for Beremin model's parameters can be obtained; if the curves do not intersect in the normal range of 5<m<40, it indicates that there is no solution for the Beremin model's parameters; if the curves are overlapped in a range of m (usually a range of 5<m<40), it indicates that there are equivalent solutions for m and $\sigma_u$. The calibration method in the invention can determine the Beremin model's parameters simultaneously from different types of specimens (≥two types of specimens) in one calibration diagram, and can be readily applied to the study of the transferability of the calibrated parameters across structures of different constraints.

BRIEF DESCRIPTION OF THE DRAWINGS

These and other features and advantages of the present invention will become more readily appreciated when considered in connection with the following detailed description and appended drawings, wherein.

DETAILED DESCRIPTION OF THE PREFERRED EMBODIMENTS

Figure 1:
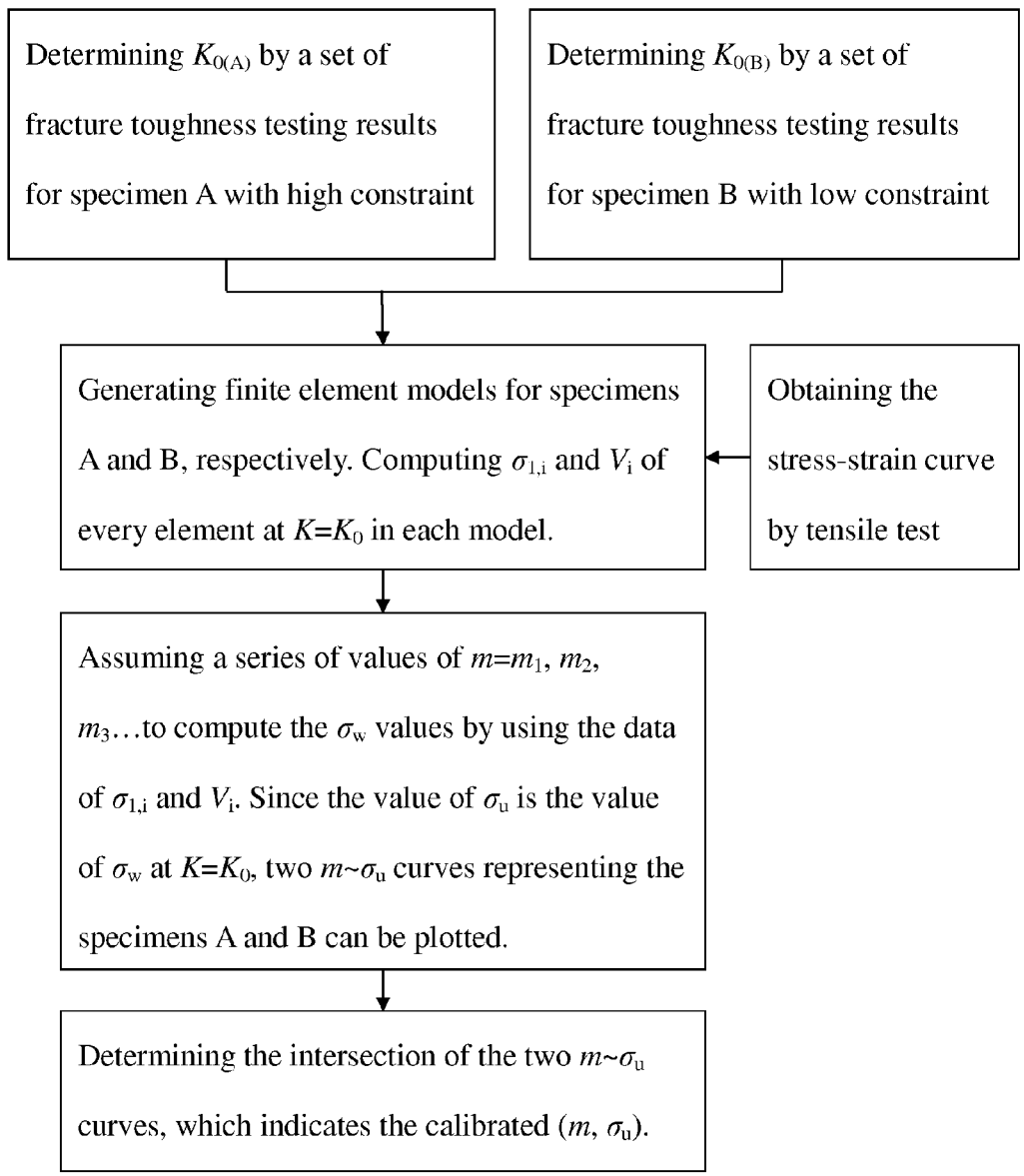
FIG. 1 is the flow diagram of the calibration method according to this invention.

The flow diagram of the calibration method for the brittle fracture assessment parameters for materials based on the Beremin model is shown in FIG. 1, and the details are described in the following:

(1) Select at least two types of specimens made of a same material but with different constraints such as high constraint specimen A and low constraint specimen B. Perform fracture toughness test using specimen A and specimen B in the ductile-to-brittle transition region to obtain two sets of fracture toughness data, $K_{Jc(k),A}$ and $K_{Jc(j),B}$ wherein k and j are the testing order numbers. Generally speaking, the more data in each set, the greater the accuracy of the brittle fracture assessment parameters, m and $\sigma_u$, from the calibration method. Therefore, each set preferably has at least 6 fracture toughness data and more preferably has at least 15 fracture toughness data. The fracture toughness values $K_{0(A)}$ and $K_{0(B)}$ corresponding to 63.2% failure probability can be determined respectively for specimens A and B at a same calibration temperature T by using the fracture toughness data.

(1.1) If the fracture toughness data $K_{Jc(k),A}$ and $K_{Jc(j),B}$ for specimens A and B are measured at the calibration temperature $T=T_A=T_B$, the fracture toughness values $K_{0(A)}$ and $K_{0(B)}$ corresponding to 63.2% failure probability at the calibration temperature can be calculated directly.

(1.2) If specimens A and B are tested at different temperatures $T_A \neq T_B$ to generate fracture toughness data $K_{Jc(k),A}$ and $K_{Jc(j),B}$, master curve for the material can be determined in accordance with ASTM E1921 proposed by the American Society for Testing and Materials, which can make the estimates of $K_0$ corresponding to 63.2% failure probability for the specimens at the calibration temperature T.

It should be noted that the estimation of fracture toughness of the two types of specimens using master curve is conducted under the assumption that brittle fracture occurs. Low constraint specimen B should be generally tested at lower temperature $T_B$, while fracture toughness test on high constraint specimen A can be performed at higher temperature $T_A$ at which specimen B may exhibit significant ductile tearing prior to cleavage fracture. Therefore, it is suggested that the fracture toughness data for high constraint specimen A should be converted to those tested at temperature $T_B$ as specimen B. According to the requirements in ASTM E1921, it is also suggested that fracture toughness test on high constraint specimen A should be performed to establish the master curve for the material such that the estimated value of $K_{0(A)}$ can be obtained at the calibration temperature $T=T_B$.

(2) Uniaxial tensile testing is carried out at the same calibration temperature T mentioned above to obtain the tensile property of the material. Perform finite element analyses for high constraint specimen A and low constraint specimen B, and then export the maximum principal stress $\sigma_{1,i}$ and element volume $V_i$ of each element at $K=K_0$ in each model, where K is a stress intensity factor that describes the intensity of far field loading on the crack front, and i is an order number of elements.

(3) Beremin model adopts a two-parameter Weibull distribution to predict the cumulative failure probability of cleavage fracture, $P_f$, for structures, as follows:

$$P_f(\sigma_w) = 1 - \exp\left[-\left(\frac{\int_{V_{pl}} \sigma_1^m dV}{\sigma_u^m V_0}\right)\right] = 1 - \exp\left[-\left(\frac{\sigma_w}{\sigma_u}\right)^m\right] \quad (1)$$

$$\text{where } \sigma_w = \sqrt[m]{\int_{pl} (\sigma_l)^m \frac{dV}{V-0}},$$

named Weibull stress, is a driving force for cleavage fracture; the Weibull slope, m, describes the scatter in the microcracks distribution and its value quantifies the degree of scatter of experimental failure data; the scale parameter of the Weibull distribution, $\sigma_u$, is related to the microscale material toughness and corresponds to the $\sigma_w$ value at $P_f=63.2\%$.

Therefore, at the level of loading $K=K_0$ corresponding to $P_f=63.2\%$, the Equation (2) is obtained:

$$\sigma_u = \sigma_w = \sqrt[m]{\int_{V_{pl}} (\sigma_1)^m \frac{dV}{V_0}} = \sqrt[m]{\sum_i^n (\sigma_{1,i})^m \frac{V_i}{V_0}} \quad (2)$$

Where $V_{pl}$ represents the fracture process region; n denotes the number of elements in the fracture process region; $\sigma_{1,i}$ and $V_i$ represent the maximum principal stress and element volume of each element in the fracture process region; $V_0$ represents a reference volume; $V_{pl}$ is defined as the region where the maximum principal stress exceeds the yield strength: $\sigma_{1,i} \geq \lambda \sigma_{ys}$, where $\lambda$ is a constant factor and is generally taken equal to 1 or 2; $\sigma_{ys}$ is the yield strength of the material at the calibration temperature T.

Assuming a series of values of the Weibull slope $m=m_1, m_2, m_3 \ldots$ etc. (The values of m are usually taken equal to integers larger than 5 and less than 40) and calculate the $\sigma_w$ for specimens A and B at $K_J=K_{0(A)}$ and $K_{0(B)}$ respectively, based on the Equation (2) using the values of $\sigma_{1,i}$ and $V_i$ obtained in step (2). Since the value of $\sigma_u$ is the value of $\sigma_w$ at $K_J=K_0$, two m~$\sigma_u$ curves are obtained as illustrated in FIG. 2, namely the characteristic curves for the Beremin model's parameters.

Figure 2:
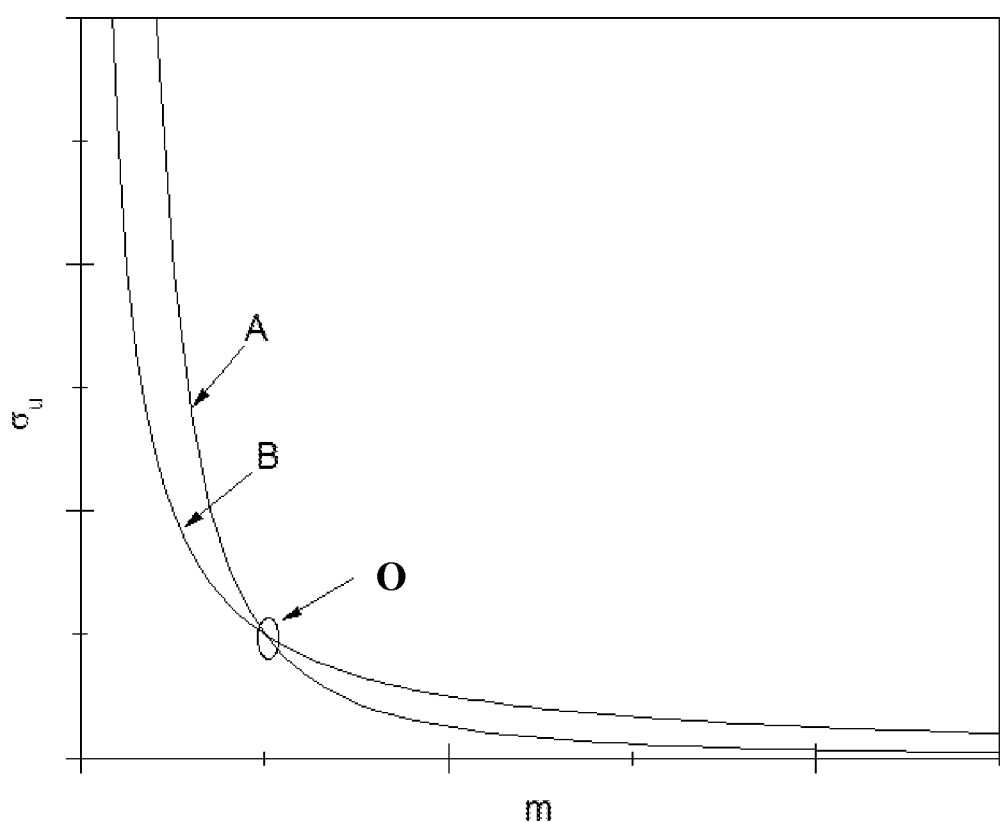
FIG. 2 is the schematic drawing for the calibration method based on the m~$\sigma_u$ curves intersection.

(4) Find the intersection of the two m~$\sigma_u$ curves marked with "O" as illustrated in FIG. 2 and determine the values of the brittle fracture assessment parameters (m, $\sigma_u$) for the material by the coordinate of the intersection point.

The following is the details of the present invention in specific embodiments. The attention must be paid that the examples are only used for the purpose of illustration, not to limit the scope of the invention.

EXAMPLE 1

The material is a homemade C—Mn steel 16MnR which is widely used for manufacturing pressure vessels in China. Select three-point bend specimen with thickness of 0.5 inches (0.5T-SE(B) specimen) as the high constraint specimen. For 0.5T-SE(B) specimen, the width to thickness ratio W/B is equal to 2. Select the pre-crack Charpy size specimen (PCVN specimen) as the low constraint specimen, which has the width to thickness ratio W/B equal to 1. Both the 0.5T-SE(B) and PCVN specimens have the span to width ratio S/W=4 and the nominal crack depth ratio $a_0/W=0.5$.

The calibration method for the brittle fracture assessment parameters for materials based on the Beremin model comprises the following steps:

(1) Test the 0.5T-SE(B) and PCVN specimens at T=−100° C. to generate two sets of fracture toughness data which are listed in Tables 1 and 2. The $K_0$ values for the 0.5T-SE(B) and PCVN specimens at T=−100° C. are calculated as $K_{0(0.5T)}=126.9$ MPa√m and $K_{0(PCVN)}=208.4$ MPA√m respectively, based on the fracture toughness data $K_{Jc(0.5T)}$ and $K_{Jc(PCVN)}$ in Tables 1 and 2.

TABLE 1

| Specimen ID | $K_{Jc(0.5\ T)}$ (MPa√m) |
| --- | --- |
| 16MnR0.5T-8 | 54.5 |
| 16MnR0.5T-10 | 55.6 |
| 16MnR0.5T-5 | 103.3 |
| 16MnR0.5T-4 | 103.6 |
| 16MnR0.5T-3 | 109.1 |
| 16MnR0.5T-7 | 111.7 |
| 16MnR0.5T-12 | 121.1 |
| 16MnR0.5T-6 | 128.4 |
| 16MnR0.5T-11 | 185.6 |
| 16MnR0.5T-9 | 202.7 |

TABLE 2

| Specimen ID | $K_{Jc(PCVN)}$ (MPa√m) |
| --- | --- |
| 16MnRPCVN32 | 85.9 |
| 16MnRPCVN10 | 100.9 |
| 16MnRPCVN34 | 102.7 |
| 16MnRPCVN14 | 150.7 |
| 16MnRPCVN31 | 156.8 |
| 16MnRPCVN35 | 187.9 |
| 16MnRPCVN33 | 192.4 |
| 16MnRPCVN36 | 193.2 |
| 16MnRPCVN13 | 206.5 |
| 16MnRPCVN12 | 211.0 |
| 16MnRPCVN38 | 215.8 |
| 16MnRPCVN37 | 222.0 |
| 16MnRPCVN16 | 236.4 |
| 16MnRPCVN15 | 254.4 |
| 16MnRPCVN18 | 284.4 |
| 16MnRPCVN17 | 288.1 |

(2) Uniaxial tensile testing is carried out at −100° C. to obtain the stress-strain curve for 16MnR steel. Perform finite element analyses for the 0.5T-SE(B) and the PCVN specimens and then export the maximum principal stress, $\sigma_{1,i}$ and element volume $V_i$ of each element in each model at $K=K_0$. The fracture toughness region is defined as the region where $\sigma_{1,i} \geq \lambda \sigma_{ys}$ with $\lambda=1$.

(3) The reference volume $V_0$ is taken as $(50\ \mu m)^3$ in the example. Assume $m=6, 7, 8 \ldots, 10$ and calculate the $\sigma_w$ using the data extracted from the fracture process region. Since the value of $\sigma_u$ is the value of $\sigma_w$ at $K=K_0$, two m~$\sigma_u$ curves are obtained as illustrated in FIG. 3.

Figure 3:
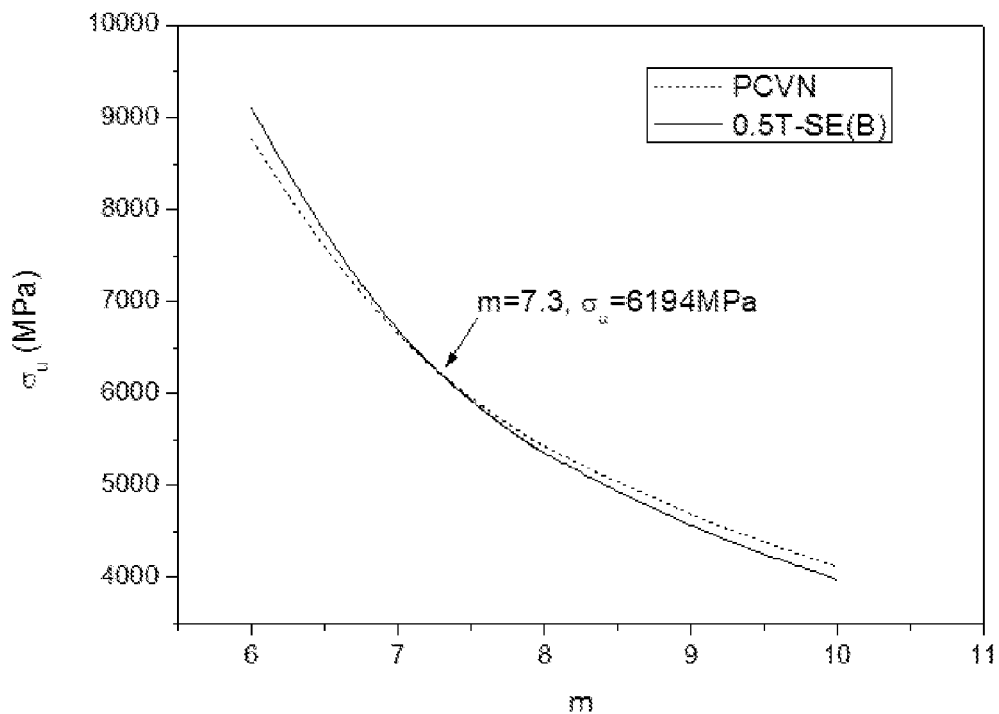
FIG. 3 shows the Beremin model's parameters for 16MnR steel according to the example 1 of this invention.

(4) Find the intersection of the two m~$\sigma_u$ curves in FIG. 3 and obtain the Beremin model's parameters, m=7.3 and $\sigma_u=6194$ MPa, for 16MnR steel, by the coordinate of the intersection point.

Figure 4:
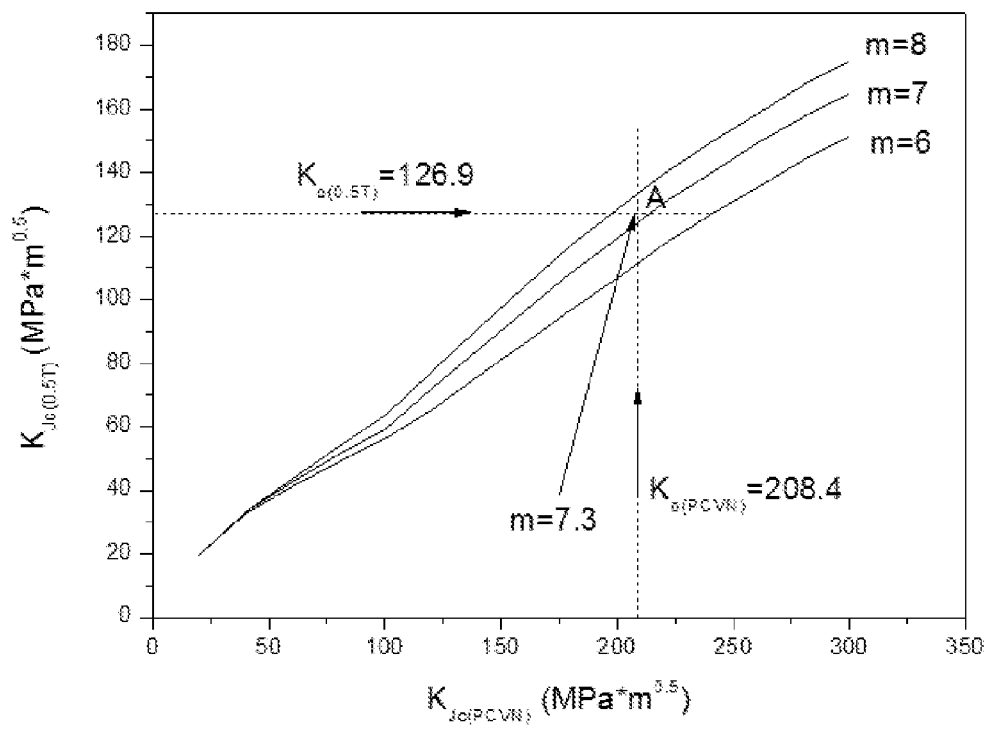
FIG. 4 shows the Beremin model's parameters for 16MnR steel according to the RGD calibration method.

RGD calibration method is applied to determine the Weibull slope m. As shown in FIG. 4, the point "A", whose ordinate is $K_{0(0.5T)}=126.9$ MPa√m and abscissa is $K_{0(PCVN)}=208.4$ MPa$\sqrt{m}$, falls in the area between the two curves corresponding to m=7 and m=8. Consequently, the Weibull slope m is calculated as 7.3 by interpolation. At $K_J=K_{0(0.5T)}$ or $K_{0(PCVN)}$, the calibrated $\sigma_u$ is calculated as 6194 MPa. The calibration results from the calibration method in this invention are exactly equal to the (m, $\sigma_u$) values obtained by the RGD procedure.

EXAMPLE 2

The material is a A508-3 forging for the construction of nuclear pressure vessels. Select three-point bend specimen with thickness of 0.5 inches (0.5T-SE (B) specimen) as the high constraint specimen. For 0.5T-SE(B) specimen, the width to thickness ratio W/B is equal to 2. Select the pre-crack Charpy size specimen (PCVN specimen) as the low constraint specimen, which has the width to thickness ratio W/B is equal to 1. Both the 0.5T-SE (B) and PCVN specimens have the span to width ratio S/W=4 and the nominal crack depth ratio $a_0/W=0.5$.

The calibration method for the brittle fracture assessment parameters for materials based on the Beremin model comprises the following steps:

(1) Test the 0.5T-SE(B) specimens at three different temperatures −81° C., −60° C. and −40° C., and test the PCVN specimens at −100° C. The fracture toughness data $K_{Jc(0.5T)}$ and $K_{Jc(PCVN)}$ are showed in Tables 3 and 4 respectively. The $K_0$ values for the PCVN specimens at T=−100° C. is calculated as $K_{0(PCVN)}=117.8$ MPa$\sqrt{m}$ by using the fracture toughness data $K_{Jc(PCVN)}$ in Table 4. The reference temperature $T_0$ of master curve is determined to be −61° C. using ASTM E1921 multi-temperature analysis procedure for the fracture toughness data for 0.5T-SE(B) specimen in Table 3. The $K_0$ value for 0.5T-SE(B) specimen at T=−100° C. is estimated to be 76.5 MPa$\sqrt{m}$ by master curve.

TABLE 3

| Temperature (° C.) | Specimen ID | $K_{Jc(0.5\ T)}$ (MPa$\sqrt{m}$) |
| --- | --- | --- |
| −81 | 3A17 | 66.4 |
|  | 3A13 | 70.1 |
|  | 3A11 | 78.0 |
|  | 3A15 | 81.2 |
|  | 3A14 | 89.6 |
|  | 3A16 | 104.2 |
|  | 3A12 | 109.8 |
| −60 | 2A13 | 110.8 |
|  | 3A1A | 112.6 |
|  | 2A11 | 113.3 |
|  | 2A12 | 126.5 |
|  | 2A14 | 142.7 |
|  | 2A15 | 147.6 |
| −40 | 3A19 | 161.1 |
|  | 3A18 | 208.6 |

TABLE 4

| Temperature (° C.) | Specimen ID | $K_{Jc(PCVN)}$ (MPa$\sqrt{m}$) |
| --- | --- | --- |
| −100 | 1A1B | 73.8 |
|  | 1A1L | 92.3 |
|  | 1A1D | 93.4 |
|  | 1A15 | 101.9 |
|  | 1A14 | 104.6 |
|  | 1A1A | 106.2 |
|  | 1A18 | 107.1 |
|  | 1A19 | 108.5 |
|  | 1A1C | 114.2 |
|  | 1A17 | 149.2 |
|  | 1A16 | 153.0 |

(2) Uniaxial tensile testing is carried out at −100° C. to obtain the stress-strain curve for A508-3 forging. Perform finite element analyses for the 0.5T-SE(B) and the PCVN specimens and then export the maximum principal stress $\sigma_{1,i}$ and element volume $V_i$ of each element in each model at $K=K_0$. The fracture toughness region is defined as the region where $\sigma_{1,i} \geq \lambda \sigma_{ys}$ with $\lambda=1$.

(3) The reference volume $V_0$ is taken as $(50\ \mu m)^3$ in the example. Assume m=10, 11, . . . , 12 and calculate the $\sigma_w$ using the data extracted from the fracture process region. Since the value of $\sigma_u$ is the value of $\sigma_w$ at $K=K_0$, two m~$\sigma_u$ curves are obtained as illustrated in FIG. 5.

Figure 5:
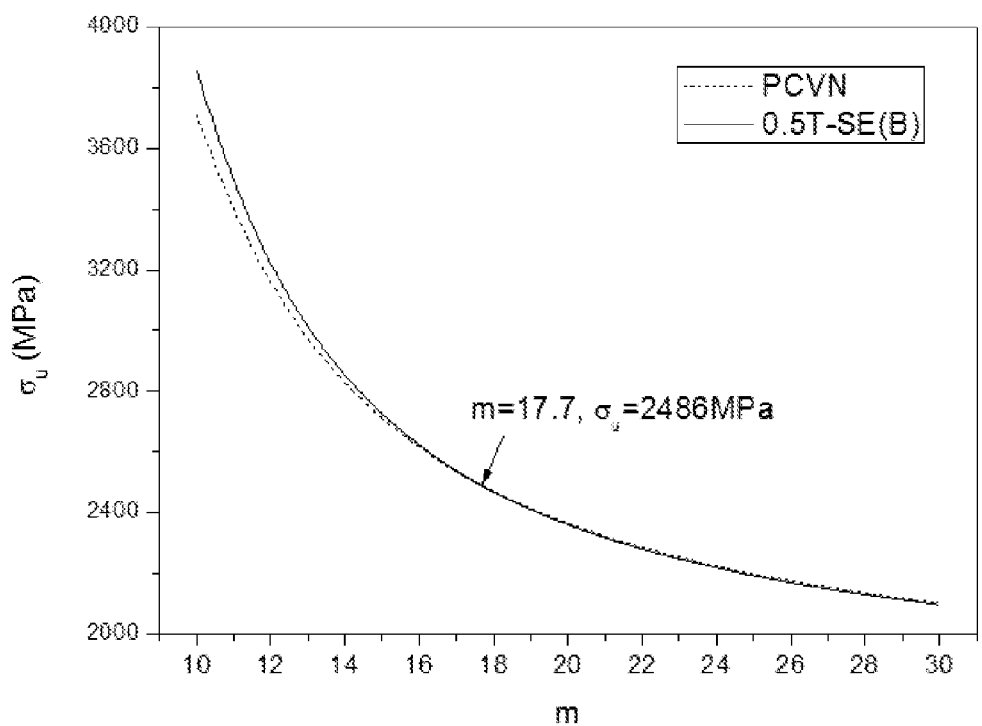
FIG. 5 shows the Beremin model's parameters for A508-3 forging according to the example 2 of this invention.

(4) Find the intersection of the two m~$\sigma_u$ curves in FIG. 5 and obtain the Beremin model's parameters, m=17.7 and $\sigma_u=2486$ MPa, for A508-3 forging, by the coordinate of the intersection point. In addition, the data point (m, $\sigma_u$) on the region where the two m~$\sigma_u$ curves are almost overlapped (16<m<30) can be taken as the equivalent solutions for the calibrated parameters.

Figure 6:
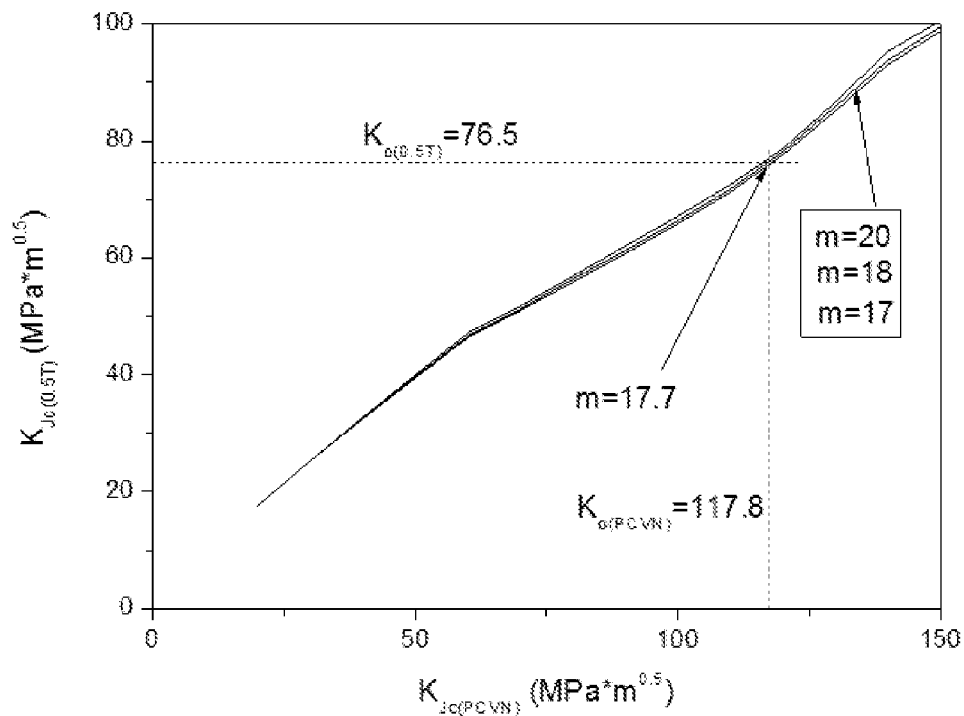
FIG. 6 shows the Beremin model's parameters for A508-3 forging according to the RGD calibration method.

RGD calibration method is applied to determine the Weibull slope m. As shown in FIG. 6, the Weibull slope m is calculated as 17.7 by interpolation. At $K_J=K_{0(0.5T)}$ or $K_{0(PCVN)}$, the calibrated $\sigma_u$ is calculated to be 2486 MPa.

The calibration method proposed in the invention eliminates the redundant calculations of the $\sigma_w$ and the toughness scaling based on equal $\sigma_w$ values in the case of $K_J \neq K_0$. With a series of assumed m values, the $\sigma_w$ values are calculate only at $K=K_0$ in the corresponding specimen to construct m~$\sigma_u$ curves for the specimens of different constraints. The calibrated values of m and $\sigma_u$ are simultaneously obtained through the intersection of the m~$\sigma_u$ curves. It can be observed from the above examples that the calibration method in the present invention has much lower computational cost compared with the RGD calibration method and the same calibration accuracy as the RGD calibration method.

Compared with the RGD calibration method (FIG. 4 and FIG. 6), the calibration method of the present invention visually displays the calibration process as illustrated in FIG. 3 and FIG. 5. The solutions for (m, $\sigma_u$) can be decided by the different cases of intersection of m~$\sigma_u$ curves. FIG. 3 and FIG. 5 show that the pair of m~$\sigma_u$ curves for 16MnR are overlapped in a specific range, and so are the pair of m~$\sigma_u$ curves for A508-3 forging. According to the argument of the proposed calibration method, it indicates that there are equivalent pairs of (m, $\sigma_u$) for toughness scaling across different constraint structures, especially the example 2. The RGD calibration method may neglect the equivalent solutions for (m, $\sigma_u$), but only yield the most accurate one.

What is claimed is:

1. A calibration method for the brittle fracture assessment parameters for materials based on the Beremin model, the method comprises the following steps:

(1) Selecting at least two types of specimens made of a same material but with different constraints, and calculating the fracture toughness value $K_0$ corresponding to 63.2% failure probability for each type of specimens at a same calibration temperature by using the respective fracture toughness data;

(2) Constructing finite element models for each type of specimens using the stress-strain curve of the material measured at the same calibration temperature, and calculating the maximum principal stress $\sigma_{1,i}$ and element volume Vi of each element at $K=K_0$ in each model, where K is a stress intensity factor that describes the intensity of far field loading on the crack front, and i is an order number of elements;

(3) Assuming a series of values of the Weibull slope m and calculating a set of values of the Weibull scale parameter $\sigma_u$ for each type of specimens according to the following equation, and plotting the Beremin's parameters characteristic curves for each type of specimens with the curves representing the relationship between m and $\sigma_u$ for each type of specimens;

$$\sigma_u = \sqrt[m]{\sum_i^n (\sigma_{1,i})^m \frac{V_i}{V_0}}$$

wherein, n represents the number of elements in the fracture process region, $V_0$ represents a reference volume;

(4) Determining the brittle fracture assessment parameters for the material according to the coordinates of the intersection of the Beremin's parameters characteristic curves;

(5) using the brittle fracture assessment parameters in safety engineering.

2. The calibration method for the brittle fracture assessment parameters for materials based on the Beremin model according to claim 1, wherein, in the step (1), fracture toughness tests on each type of specimens are carried out at the same calibration temperature to obtain the fracture toughness data.

3. The calibration method for the brittle fracture assessment parameters for materials based on the Beremin model according to claim 1 wherein, in the step (1), fracture toughness tests are carried out on each type of specimens at different temperatures to obtain the fracture toughness data, and calculating the fracture toughness value $K_0$ corresponding to 63.2% failure probability at the same calibration temperature by using the predetermined master curve.

4. The calibration method for the brittle fracture assessment parameters for materials based on the Beremin model according to claim 3 wherein, in the step (1), the same calibration temperature is the lowest of the different temperatures.

5. The calibration method for the brittle fracture assessment parameters for materials based on the Beremin model according to claim 1 wherein, in the step (2), the uniaxial tensile test is carried out at the same calibration temperature to obtain the stress-strain curve.

6. The calibration method for the brittle fracture assessment parameters for materials based on the Beremin model according to claim 5 wherein, in the step (3), the values of m are taken as integers larger than 5 and less than 40.

7. The calibration method for the brittle fracture assessment parameters for materials based on the Beremin model according to claim 6 wherein, in the step (3), the fracture process region is defined as the volume inside the loci $\sigma_{1,i} \geq \lambda \sigma_{ys}$, wherein $\lambda$ is a constant, $\sigma_{ys}$ is the yield strength of the material at the calibration temperature.

8. The calibration method for the brittle fracture assessment parameters for materials based on the Beremin model according to claim 7 wherein, in the step (3), the value of $\lambda$ is 1 or 2.

9. The calibration method for the brittle fracture assessment parameters for materials based on the Beremin model according to claim 1 wherein, in the step (1), at least six fracture toughness data are obtained for each type of specimens are required.

10. The calibration method for the brittle fracture assessment parameters for materials based on the Beremin model according to claim 9 wherein, in the step (1), at least fifteen fracture toughness data are obtained for each type of specimens are required.

* * * * *